United States Patent
Burton et al.

(10) Patent No.: US 6,303,591 B1
(45) Date of Patent: Oct. 16, 2001

(54) 21-HYDROXY-6,19-OXIDOPROGESTERONE (21OH-6OP) AND ITS USE AS MEDICAMENT FOR TREATING EXCESS OF GLUCOCORTICOIDS

(75) Inventors: Gerardo Burton, Provincia de Buenos Aires; Carlos Pedro Lantos, Buenos Aires, both of (AR)

(73) Assignee: Applied Research Systems ARS Holding NV (CH)

(*) Notice: Subject to any disclaimer, the term of this patent is extended or adjusted under 35 U.S.C. 154(b) by 0 days.

(21) Appl. No.: 09/533,225

(22) Filed: Mar. 23, 2000

Related U.S. Application Data

(63) Continuation of application No. PCT/EP98/06021, filed on Sep. 22, 1998.

(30) Foreign Application Priority Data

Sep. 23, 1997 (EP) .................................................. 97116526

(51) Int. Cl.⁷ .................................................. A61K 31/56
(52) U.S. Cl. .................................................. 514/179
(58) Field of Search .................................................. 514/179

(56) References Cited

U.S. PATENT DOCUMENTS 6,150,349 * 11/2000 Schatzberg et al. .................. 514/179

FOREIGN PATENT DOCUMENTS

| | | |
|---|---|---|
| 0763541 | 3/1997 | (EP) . |
| 0763541A1 | 3/1997 | (EP) . |

OTHER PUBLICATIONS

"RU–26988—A New Tool for the Study of Mineralcorticoid Receptor"; Gomez–Sanchez, et al.; *Endocrinology*; vol. 113, No. 3 pp. 1004–1009.

"Glucocorticoid Receptors"; Funder; *J. Steroid Biochem. Molec. Biol.*; vol. 43, No. 5, pp. 389–394.

"Ligand Properties of 11,19–Oxido Progesterone. A Preliminary Report"; Galigniana, et al.; *An. Assoc. Quim. Argent*; 81:333–340 (1993).

"Renal Mineralocorticoid Receptors and Hippocampal Corticosterone–Binding Species Have Identical Intrinsic Steroid Specificity"; Krozowski, et al.; *Proc. Natl. Acad. Sci. USA*; vol. 80; 80; pp. 6056–6060; Oct. 1983.

"Transcortin in Rat Kidney: Subcellular Distribution of Transcortin–Synthesizing Polyribosomes"; Kraujelis, et al.; *J. Steroid Biochem. Molec. Biol.*; vol. 38; No. 1; pp. 43–47; 1991.

"Sodium–Retaining Activity of Some Natural and Synthetic 21–Deoxysteroids"; G. Burton, et al.; *Molecular Pharmacology*; 47:535–543; 1995.

"21–Hydroxy–6, 19–oxidoprogesterone: A Novel Synthetic Steroid with Specific Antiglucocorticoid Properties in the Rat"; G.P. Vincent, et al. *Molecular Pharmacology*, 52; 749–753 (1997).

"Primary structure and expression of functional human glucocorticoid receptor DNA"; S. M. Hollenberg, et al.; *Nature*; vol. 318 19/26; Dec. 1985; pp. 635–641.

"Nuclear Hormone Receptors Activate Direct, Inverted, and Everted Repeats"; B. M. Forman, et al.; *Ann. N.Y. Acad. Sci.* 761:29–37 (1995).

"Structure–Activity Relationship in Certain Glucocorticoids and Mineralocorticoids"; C. P. Lantos, et al.; *Mechanisms of Hormone Action*; pp. 477–494; 1991.

"Molecular Conformation and Protein Binding Affinity of Progestins"; W. L. Duax, et al.; *Journal of Toxicology and Environmental Health*; 4:205–277, 1978.

"General Structure–Activity Correlations of Antihormones"; G. Teutsch, et al,; *Ann. N.Y. Acad. Sci*; 761: 5–28 (1995).

"Cloning of Human Mineralocorticoid Receptor Complementary DNA: Structural and Funcational Kinship with the Glucocorticoid Receptor"; J. L. Arriza, et al.; *Science*; vol. 237; Jul. 17, 1987; pp. 268–275.

"A new synthetic, high specific ligand for mineralcorticoid receptor determination"; Grill, et al.; *J. Steroid Biochem.* 23–Sppl., 19S (1985).

"ZK91587: A novel synthetic antimineralocorticoid displays high affinity for corticosterone (Type I) receptors in the rat hippocampus"; Sutanto, et al.; *Life Sciences*, 43:1537–1543 (1988).

"RU38486: A potent antiglucocorticoid in vivo"; Philibert, et al.; *IIIV International Congress of Pharmacology*; Tokyo, Japan; Abstract (1981).

"Mifepristone (RU486)—A Modulator of Progestin and Glucocorticoid Action"; Spitz, et al.; *The New England Journal of Medicine*; vol. 329; No. 6; Aug. 5, 1993; pp. 404–412.

"An Improved Preparation of 11,19–Oxidopregn–4–ene–3, 20–dione and 6,19–Oxidopregn–4–ene–3,11,20–trione" Brachet–Cota, et al.; Z.Naturforsch.Teil (B) 45:711–715 (1990).

"Synthesis of 21–hydroxy–11,19–oxidopregn–4–ene–3, 20–dione and 21–hydroxy–6,19–oxidopregn–4–ene–3,2—dione"; Veleiro, et al.; *Steroids*; 60:268–271, 1995.

(List continued on next page.)

Primary Examiner—James H. Reamer
(74) Attorney, Agent, or Firm—Ostrolenk, Faber, Gerb & Soffen, LLP

(57) ABSTRACT

The comformationally highly bent steroid 21-hydroxy-6,19-oxidoprogesterone (21OH-6OP) has been found to be a selective antiglucocoriticoid virtually lacking mineralocorticoid or glucocorticoid properties as well as affinity for MR or PR and is used for the treating of diseases associated with an excess of glucocordcoids in the body, such as the Cushing's syndrome or depression.

5 Claims, 5 Drawing Sheets

OTHER PUBLICATIONS

"Features of the shuttle pair 11β–hydroxyprogesterone–11–ketoprogesterone"; Galigniana, et al.; *Steroids*; 62:358–364, 1997.

"Stability Study on Renal Type I Mineralocorticoid Receptor"; Galigniana; *Life Sciences*; vol. 59, No. 7, pp. 511–521; 1996.

"Effect of Oestradiol Benzoate, Tamoxifen and Monohydroxytamoxifen on Immature Rat Uterine Progesterone Receptor Synthesis and Endometrial Cell Division"; V.C. Jordan, et al.; *Journal of Steroid Biochemistry*; vol. 11, pp. 285–291; 1979.

"A Method for the Colorimetric Estimation of Glycogen with Iodine"; Krisman; *Analytical Biochemistry*; 4, 17–23 (1962).

"The Enzymic Isolation of Adult Rat Hepatocytes in a Functional and Viable State"; Fry, et al.; *Analytical Biochemistry*; 71, 341–350 (1976).

"Tyrosine Aminotransferase (Rat Liver)"; Granner, et al.; *Methods in Enzymology*; 17–A:633–637 (1975).

Burton, et al., "Sodium–Retaining Activity of Some Natural and Synthetic 21–deoxysteroids", *Molecular Pharmacology*, vol. 47, 1995, pp. 535–543.

Burton, et al., "21–hydroxy–6, 19–oxidoprogesterone: A Novel Synthetic Steroid With Specific Antiglucocorticoid Properties in the Rats", *Mol. Pharmacol.*, vol. 52, No. 4, Oct. 1997, pp. 749–753.

\* cited by examiner

21-HYDROXY-6,19-OXIDOPROGESTERONE (21OH-6OP) AND ITS USE AS MEDICAMENT FOR TREATING EXCESS OF GLUCOCORTICOIDS

CROSS-REFERENCE TO RELATED APPLICATIONS

This is a continuation application of International Application PCT/EP98/06021, with an International filing date of Sep. 22, 1998.

The present invention relates to the use of pure antiglucocorticoids for the treatment or profilaxis of diseases associated to an excess of glucocorticoids. In particular, the invention relates to the use of 21-hydroy-6,19-oxidoprogesterone (21OH-6OP) for treating Cushing's syndrome or depression.

Cushing's syndrome or pituitary basophilism is a disorder resulting from increased adrenocortical secretion of cortisol. Hyperfunction of the adrenal cortex may be ACTH-dependent or it may be independent of ACTH regulation, eg, production of cortisol by an adrenocortical adenoma or carcinoma. The administration of supraphysiologic quantities of exogenous cortisol or related synthetic analogs suppresses adrenocortical function and mimics ACTH-independent hyperfunction. ACTH-dependent hyperfunction of the adrenal cortex may be due to hypersecretion of ACTH by the pituitary, secretion of ACTH by a nonpituitary tumor such as small cell carcinoma of the lung (the ectopic ACTH syndrome), or administration of exogenous ACTH. While the term Cushing's syndrome has been applied to the clinical picture resulting from cortisol excess regardless of the cause, hyperfunction of the adrenal cortex resulting from pituitary ACTH excess has frequently been referred to as Cushing's disease, implying a particular physiologic abnormality. Patients with Cushing's disease may have a basophilic adenoma of the pituitary or a chromophobe adenoma. Microadenomas can usually be visualized by CT or, preferably, MRI scan, using a high-resolution technique augmented by gadolinium. Some microadenomas are difficult to visualize even with these modalities. In some cases, no histologic abnormality is found in the pituitary despite clear evidence of ACTH overproduction.

Reference to Cushing's syndrome is herein intended to mean the clinical picture resulting from cortisol excess regardless of the cause, which may be also iatrogenic, both by the injection of ACTH or by the direct administration of cortisol or synthetic analogs such as prednisone, prednisolone, dexamethasone or others that are widely used in various types of diseases including allergic, asthmatic, inflammatory or immunologic. Cushing's syndrome includes in addition adrenal tumours secreting corticoids, ectopic ACTH production and Cushing's disease.

Clinical manifestations include rounded "moon" facies with a plethoric appearance. There is truncal obesity with prominent supraclavicular and dorsal cervical fat pads ("buffalo hump"); the distal extremities and fingers are usually quite slender. Muscle wasting and weakness are present. The skin is thin and atrophic, with poor wound healing and easy bruising. Purple striae may appear on the abdomen. Hypertension, renal calculi, osteoporosis, glucose intolerance, reduced resistance to infection, and psychiatric disturbances are common. Cessation of linear growth is characteristic in children. Females usually have menstrual irregularities. An increased production of androgens, in addition to cortisol, may lead to hypertichosis, temporal balding, and other signs of virilism in the female.

To-date, the only therapeutical application for antiglucocorticoids (e.g. Mifepristone) that has been attempted in a clinical setting is to treat inoperable cases of nonpituitary Cushing's syndrome. In the case of Mifepristone (both an anti-progesterone ad an anti-glucocorticoid), a very high dose (20–800 mg per day) is needed for the effectiveness in this indication.

The glucocorticoid receptor (GR), cloned in 1985 (1), is member of a protein super family of closely related intracellular receptors which function as ligand-activated transcription factors (2). Steroid ligands which are able to activate GRs and trigger a biological response exhibit a slightly torsioned steroid nucleus at the A/B-ring junction for optimal glucocorticoid (GC) activity (3,4). On the other hand, mineralocorticoid (MC) agonists require an overall flat conformation to acquire sodium-retaining activity (5). The mineralocorticoid receptor (MR), cloned by Arriza et al. (6) in 1987, showed to be highly homologus with GR. Due to that considerable homology, it was not too surprising that natural and even synthetic steroids exhibited cross-reaction between GR and MR. The progesterone receptor (PR) is the third member of a subfamily of these highly related steroid receptors. Its natural ligand, progesterone, exhibits cross-reaction with both MR and GR Employing a systematic application of strategies to increase activity and decrease crossreactivity and undesirable side effects, impressive progress has been reported in the development of new antihormonal agents with greater potency and selectivity, especially in the antiestrogen and antiandrogen fields.

The development of selective anti-corticoids is more restricted. Reference can be made to steroids of the spironolactone family which are used in therapeutics. Those inhibitors seem to belong to the class of rapidly dissociating anti-MCs (7). Another synthetic steroid described as an anti-MC, ZK91587, shows specific binding properties for kidney (8) and hippocampus type I MR (9), but not for type II GR. It may therefore be conveniently useful as a tool in the investigation of MR function in tissues containing both receptor systems.

A long-lasting search for the GC antagonist finally succeeded with the development of the 11β-aminophenyl-substituted 19-norsteroid RU38486, later shortened to RU486, in the early 80's (10). It soon became apparent, however, that this compound also possessed strong anti-progestin activity, which led to its applications as a contraceptivelcontragestive agent (11). Avoiding cross-reactions between GR and PR is still an unachieved goal for phannacologists.

We have now found that the synthetic steroid, 21-hydroxy-6,19-oxidoprogesterone (21 OH-6OP, I),

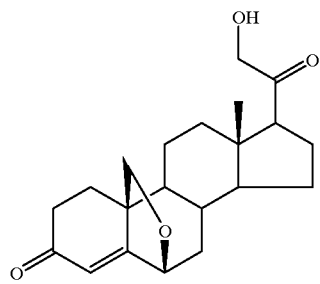

is a selective antiglucocorticoid which is unable to cross-react with uterus-PR or kidney-MR. The new structure has been developed as a result of systematic studies on MC potencies on a series of 21-deoxysteroids, among which the highly bent -6,19-oxidoprogesterone (6OP—FIG. 1) exhibited practically no Na$^+$ retaining properties (5).

Preliminary studies also showed lack of GC properties for this steroid. The 21-hydroxy introduced group into its structure conferred anti-GC properties to the 6,19-oxidopregnane skeleton.

The pure antiglucocorticoid of the present invention is, therefore, used in the treatment of diseases associated to an excess of glucocorticoids, where an antiglucocorticoid virtually lacking mineralocorticoid or glucocorticoid properties as well as affinity for MR or PR is highly desirable. In particular, the antiglucocorticoid of the present invention is used for the treatment of Cushing syndrome and depression, which are associated with an excess of glucocorticoids in the body.

The present invention, thus, provides 21-hydroxy-6,19-oxidoprogesterone of Formula I for use as a medicament.

It is a further object of the present invention the use of 21-hydroxy-6,19-oxidoprogesterone of Formula I in the manufacture of a medicament for the treatment or prophylaxis of diseases associated to an excess of glucocorticoids.

Preferably, the compound of Formula I is used in the manufacture of a medicament for the treatment of Cushing's syndrome, iatrogenic hypercortisolism or depression.

The compound of Formula I may be formulated in accordance with usual steroid formulations with one or more suitable carriers thereof.

Hatched bars represent incubations performed in the presence of vehicle instead of agonist. Only TAT stimulation by DXM and B in incubations marked with asterisk (control and +6OP) are significantly different (P<0.01) from the basal activity. Results show means ±SEM (n=4).

Figure 5:
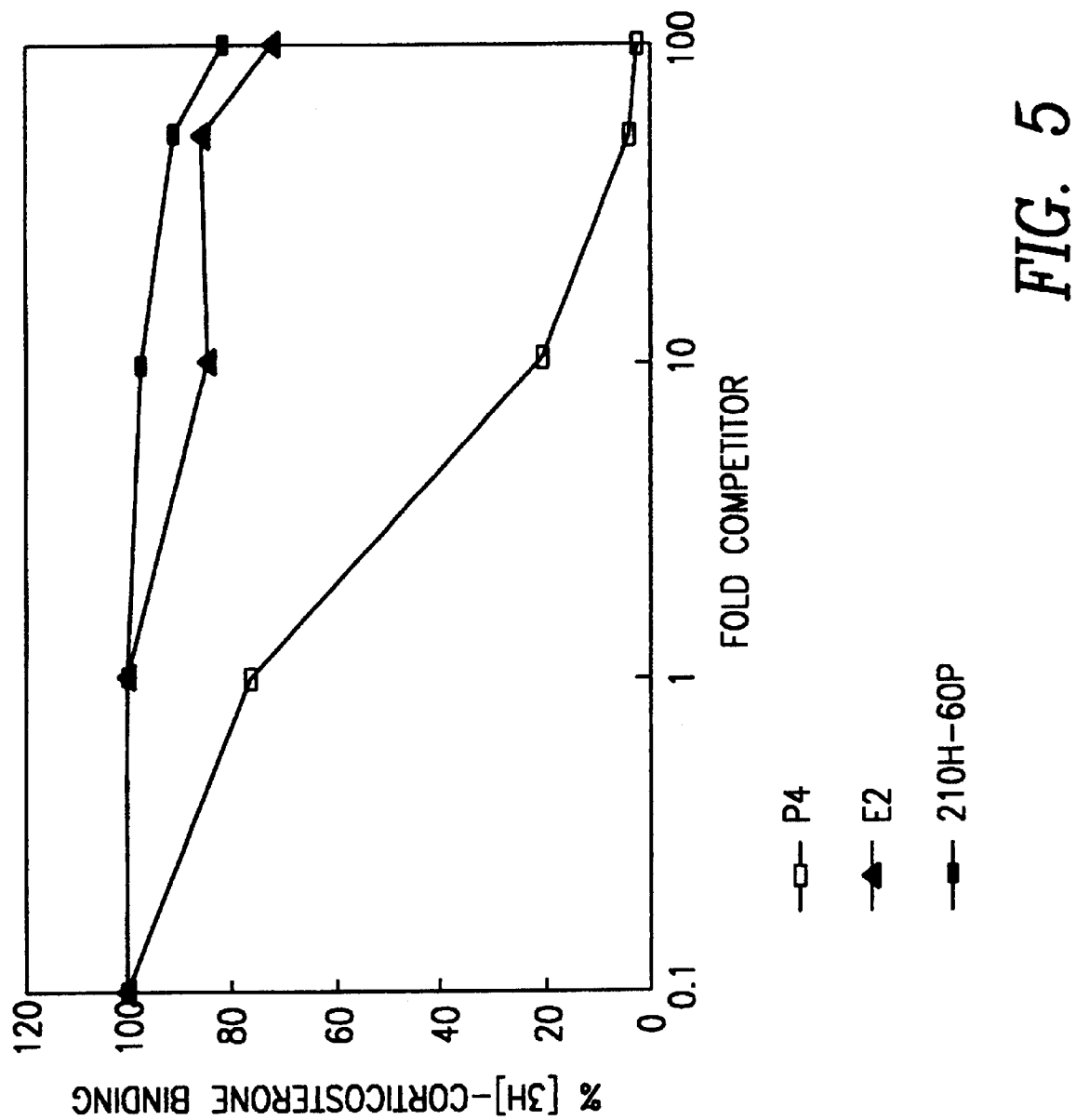

FIG. 5: 21OH-6OP does not cross-react with progesterone receptor: ($^3$H)-P$_4$ binding to uterus cytosols (2.5 mg protein/ml) in TEGM was performed according to Jordan and Dix (16) for 12 h at 0° C., in the presence of different amounts of unlabelled competitors.

The invention will now be described, by way of illustration only, with reference to the following examples:

EXAMPLE 1
MATERIALS AND METHODS

Reagents. Aldosterone (ALDO), corticosterone (B), progesterone (P$_4$), and dexamethasone (DXM) were purchased from Sigma Chemical Co. (St. Louis, Mo.). 6,19-oxidoprogesterone (6OP) and its 21-hydroxylated derivative (21OH-6OP) (Formula 1) were synthesized as previously described (12) and (13), respectively. ($^3$H)-Corticosterone (S.A.—80 Ci/mmol), ($^3$H)-ALDO S.A.=59 Ci/mmol), ($^3$H)-P, (S.A.=90 Ci/mmol), and ($^3$H)-ZK91587 (S.A.=86.5 Ci/mmol) were purchased from New England Nuclear (Boston, Mass.). RU28362 was received from Rousse[]VUclaf (Romainville, France). All reagents used were analytical grade.

Binding Assay: Adrenalectomized male Sprague-Dawley rats were bled to death by heart puncture. Cold 0.9% NaCl was injected profusely through the aorta until organs were completely blanched. Thymuses were used as a source of GR and kidneys as a source of MR. Homogenization and incubation conditions were performed as previously described, (14) and (15), respectively. Briefly, homogenates performed in cold TEGM buffer at pH 7.4 (0.1 M Tris-HCl, 10 mM EDTA, 10 mM α-mercaptoethanol, 20 mM Na$_2$MoO$_4$, 25% glycerol, 0.1 mM PMSF, 2.0 TIU/ml aprotinin and 1 mg% Leupeptin) were centrifuged at 37,000 rev. for 30 min at 0° C. Supernatants from this centrifugation are referred to as "cytosol". Thymus or kidney cytosols were incubated 12 h at 0° C. in the presence of 5 nM ($^3$H)-B or ($^3$H)-ALDO, and increasing amounts of unlabelled steroids. ($^3$H)-P$_4$ binding to uterus PR was assayed on immature female rats according to Jordan et al (16).

1.0 $\mu$M RU28362 was added to kidney- cytosols to impede ($^3$H)-ALDO cross-reacting with GR, and 1 $\mu$M cortisol (F), to uterus- cytosols to prevent (3H)-P$_4$ cross-reactions with GR and transcortin (CBG). Relative binding affinity (RBA) for partially purified CBG was determined by steroid competition for ($^3$H)-B binding as described previously (14).

Bioassay : Liver glycogen deposition was measured on adrenalectoniized male Sprague-Dawley rats (180–220 g) as follows: steroids were dissolved in ethanol/propylene glycol/0.9% NaCl solution (3:3:34) and 100 $\mu$g steroid/l00 g body weight were injected i.m. the previous night. On the morning of the experiment this dose was reinjected intraperitoneally. Three hours later the rats were killed by cervical dislocation and livers were immediately removed. Glycogen purification and quantification were carried out according to Krisman's method (17). Na$^+$-retaining properties were measured as described (5). Tyrosine aminotransferase (TAT) was induced in rat hepatocytes isolated by the procedure of Fry et al (18). TAT activity was determined according to Granner and Tomkins (19).

RESULTS

Figure 1:
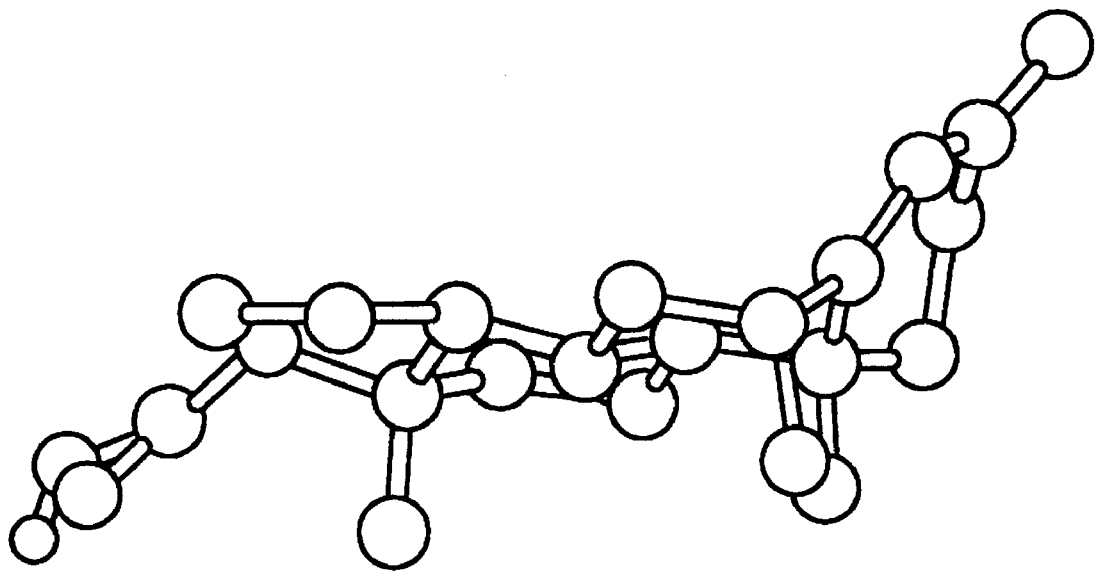
FIG. 1: Most stable conformer of 21-hydroxy-6,19-oxidoprogesterone (21OH-6OP): Geometry optimizations were carried out with AMPAC 5.0 (Semichem) using the AMI semiempirical method.
Figure 2A:
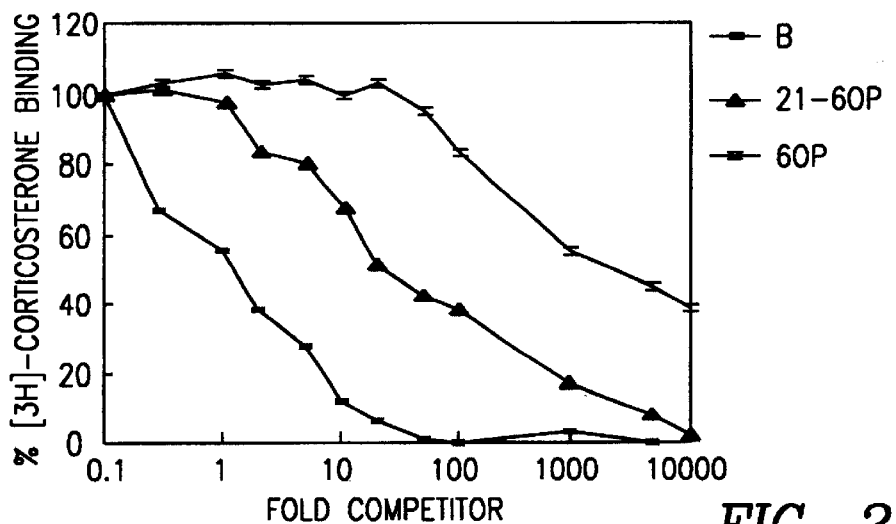
FIG. 2: Binding Properties of 21OH-6OP: Displacement curves of 5 nM ($^3$H)-B and increasing amounts of unlabelled steroid were performed for 12 h at 0° C. using the following binding proteins: Panel A: thymus cytosol (6.0 mg protein/ml); Panel B: partially purified (Example 1, Materials and Methods) CBG (1 mg protein/ml); Panel C: shows the competition of unlabelled steroids with 5 nM ($^3$H)-ALDO for kidney cytosol (10 mg protein/ml) in the presence of 1.0 $\mu$M RU28362 to prevent cross-reactions with GRs.
Figure 2B:
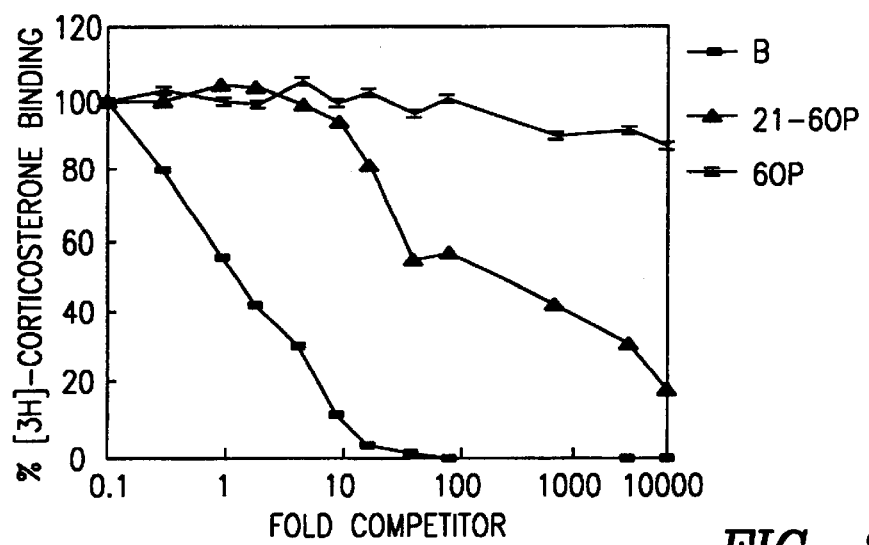
Figure 2C:
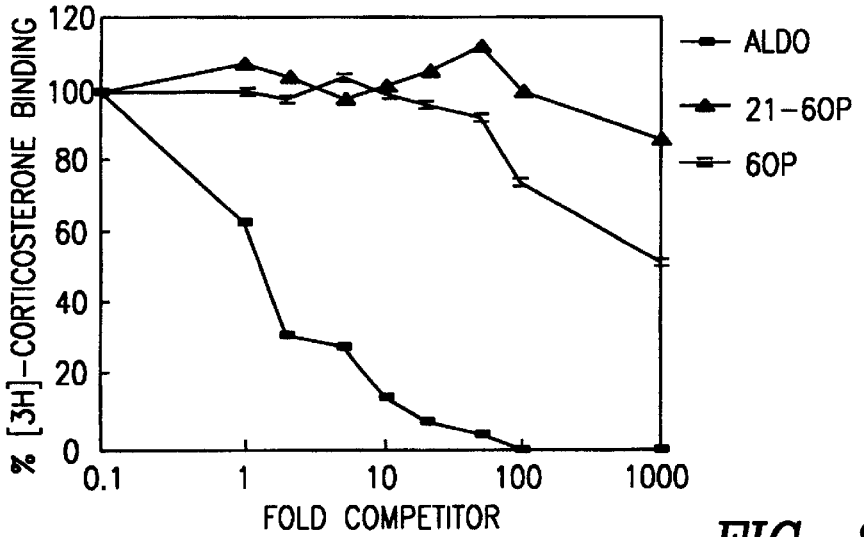

FIG. 2 shows the binding properties of 21 OH-6OP to GR from rat thymus (panel A), CBG partially purified from rat plasma (panel B), and MR from rat kidney (panel C). The displacement curve of 6,19-oxidoprogesterone is included for comparative purposes.

This steroid exhibits a moderate RBA for GR (125 nM) and a low RBA for CBG (1.27 μM). (Kd values in parentheses). It does not compete efficiently with ($^3$H)-ALDO for MR, even when a thousand fold excess was added. The introduction of a functional hydroxyl group at 21 increased binding properties of 6OP to GR over 40 times, and binding to CBG, hundred times. This introduction does not improve the binding of the 6,19-oxidopregnane skeleton to MR, (panel 2-C).

Figure 3A:
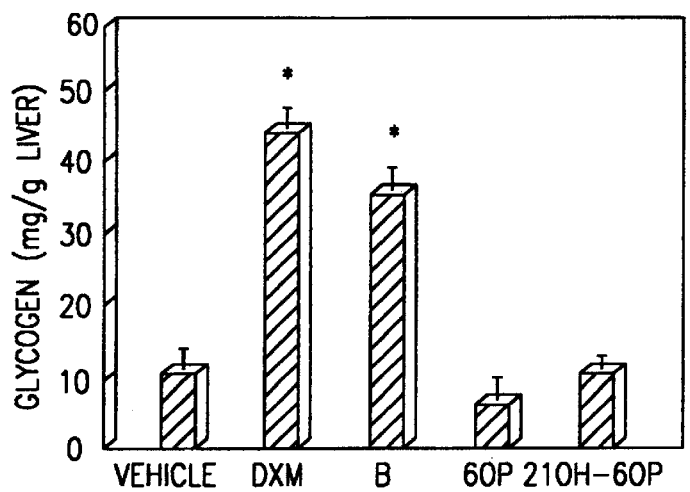
FIG. 3: Biological Properties of 21OH-6OP: A) Glycogen storage in vivo: 100 $\mu$g steroid/100 g body weight of male rats were injected as indicated in Example 1. Liver glycogen was purified and quantified with Krisman's reagent (17). Controls were injected with vehicle. Results are expressed as means±SEM (n=6). (*): different from controls P<0.02. B) TAT induction in vitro: rat hepatocytes were incubated for 5 h in HAM-F12 medium in the presence of 100 nM steroid and TAT activity was measured. Results are expressed as percentage of enzyme activity (means±SEM, n=4) over controls incubated in the presence of vehicle. (*) different from controls P<0.01. C) Sodium-retaining activity: adrenalectomized rats were treated with the indicated dose of steroids. Results are expressed as the ratio of sodium-excretion rates of steroid-injected animals to the excretion rates of rats injected with vehicle. The figure shows one representative experiment performed with five rats per dose assayed.
Figure 3B:
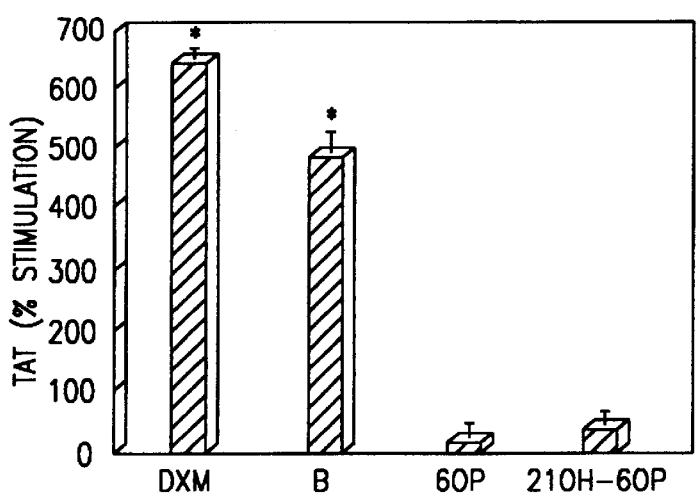
Figure 3C:
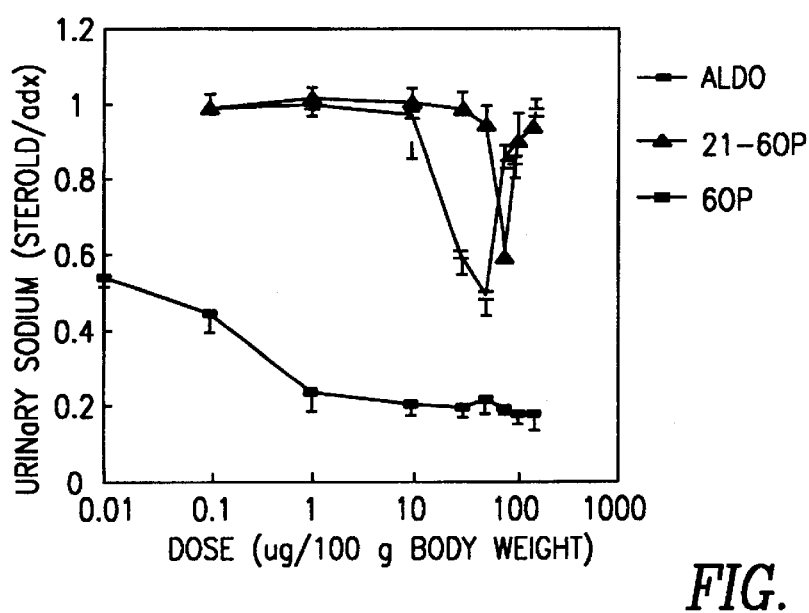

FIG. 3 shows biological properties using in vitro as well as in vivo methodology. Compared to ADX controls, DXM or B produce between three and four times more liver glycogen deposits and increases by a factor of five to is times TAT activity. In site of increasing RBA for GR, the 21-hydroxylation was unable to trigger GC-responses. In effect, FIGS. 3-A and 3-B show the neither 6OP nor 21OH-6OP evoke these responses. 21OH-6OP is almost devoid of MC properties compared with the already weak Na$^+$-retainer 6OP (FIG. 3-C). Like other weak Na$^+$ retainers, 6OP and 21 OH-6OP exhibit a parabolic dose-response function with maxima of 40% retention for 21OH-6OP and 50% for 6OP at high doses, then loosing activity at still higher doses (see also 51).

To study the binding of ALDO to kidney- MR without the competitive influence of the relatively more abundant GR, GR was removed with the specific ligand RU28362 (7). This avoided ALDO cross-reacting with GR and hence a two slope Scatchard plot (20–22).

The presence of 1.0 μM RU28862 reduces the plot to a single line corresponding to type I sites, as does the selective ligand for MR, ZK91587. The calculated Kd for type I sites in different conditions ranges between 0.4 and 1 nM (Table 1) which is at least eighty times higher than the affinity for type II sites. When the novel synthetic steroid 21OH-6OP was added to incubations performed in the presence of ($^3$H)-ALDO, a single binding site with kinetic parameters compatible with MR was again observed. This suggests that 2.5 μM 21OH-6OP is able to mask the cross reaction of ($^3$H)-ALDO with GR. Hill's coefficients ($n_g$) calculated for each condition suggest a lack of allosteric interaction (Table 1).

Figure 4:
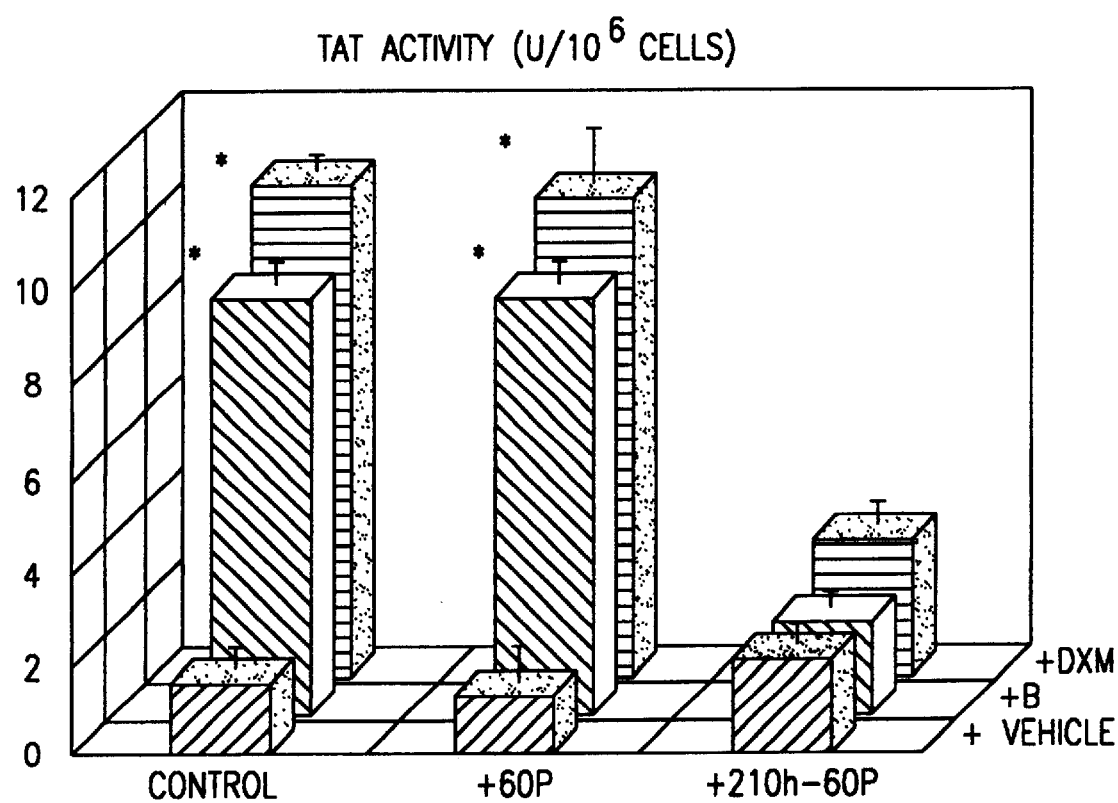
FIG. 4: 21OH-6OP shows antagonist effect on TAT induction: TAT activity was induced in hepatocytes by 100 nM DXM (black bars) or 100 nM B (white bars), in the absence (control) or in presence of 2.5 $\mu$M 6OP (+6OP) or 21OH-6OP (+21OH-6OP).

In agreement with these binding properties, an antagonistic effect of 21OH-6OP against GC was observed, Indeed, FIG. 4 shows the novel pregnanesteroid to antagonize TAT induction by corticosterone and decamethasone. The basal TAT activity in hepatocytes, denominated control in the figure, was measured by adding vehicle (final concentration: 0.2% ethanol) to the culture. Neither 6OP nor 21OH-6OP facilitate TAT induction (hatched bars) but 100 nM B (white bars) and 100 nM DXM (black bars) stimulate enzyme activity between five and six times. 2.5 μM 21OH-6OP inhibits 80% of TAT induction when concubated with B or DXM.

FIG. 5 shows that 21OH-6OP displaces ($^3$H)-P$_4$ from uterus- receptors as weakly as the negative control 17β-estradiol E$_2$). Unlabelled P$_4$, in contrast, was able to displace the tracer efficiently.

The above data demonstrate that 21-hydroxy-6,19-oxidoprogesterone is also a useful tool to study steroid-receptor interactions in systems in which more than one type of receptors is present. The RBA for GR refers to the mean affinity of (3H) in thymus cytosols (125 nM). In spite of this moderate affinity, 21OH-6OP showed no ability to interact with MR nor PR It was also able to block type II receptors in kidney cytosols where GR coexists not only with MR, but also with a high level of BG of dual origin (an unavoidable contamination by plasma (22, 23) and biosynthesis by the kidney (24). FIG. 2-B indicated that 2.5 μM 21OH-6OP can simultaneously block almost 60% of the CBG binding sites. FIG. 2 a shows only 75% of tracer displacement instead of the 95% saturation predicted according to mass action, probably because of that CBG of dual origin acting as a competitor for GR (22,23).

The induction of TAT activity in hepatocytes, triggered by both B and DXM, was be significantly inhibited by 21OH-6OP, indicating that this novel steroid is potent GC antagonist. As it does not cross-react with PR (FIG. 5), the oxidopregnansteroid is a potent selective GR blocking agent. Since most of the antiprogestins and antiglucocorticoids available cross-react with other receptors (7), the pure anti-GC steroid of Formula I has been desired for a long time for the treatment of diseases, such as the Cushing's syndrome and depression, where a selective, pure antiglucocorticoid is needed to antagonize the excess of glucocorticoids which characterize these disorders.

TABLE 1

Dissociation constants, apparent number of sites and Hill coefficients for type I receptors in the presence of RU-28362 and 21OH-6OP.

| TRACER | RECEPTOR TYPE | IN THE PRESENCE OF | Kd (nM) | Q (fmol/mg) | $n_H$ |
|---|---|---|---|---|---|
| ($^3$H)-ZK91587 | I | — | 0.42 | 98 | 0.91 |
| ($^3$H)-ALDO | I | — | 0.44 | 104 | 0.97 |
| ($^3$H)-ALDO | I | 10 μM RU-28362 | 0.72 | 124.4 | 0.90 |
| ($^3$H)-ALDO | I | 2.5 μM 21OH-6OP | 0.80 | 110 | 0.88 |
| ($^3$H)-ALDO | II | — | 64.4 | 2900 | 0.86 |

I: Type I sites
II: Type II sites

REFERENCES (1) Hollemberg S. M., C. Weinberger, E. S. Ong, G. Ceseli, A. Oro, R. Lebo, E. B. Thompson, M. G. Rosenfeld, and R. M. Evans. Primary structure and expression of a functional human glucocorticoid receptor cDNA. Nature 318: 635–641 (1985).

(2) Forman B. M. and R. M. Evans. Nuclear hormone receptors activate direct, inverted, and repeats. Ann. N. Y. Acad. Sci. 761: 29-:17 (1995).

(3) Lantos C. P., G. Burton, A. Roldan, M. C. Damasco, and A. Aragones. Structure-activity relationship in certain glucocorticoids and mineralocorticoids, in Physiopothology of Endocrine Diseases and Mechanism of Hormone Action (R. J. Soto, A. de Nicola, and J. Blaquier, eds.). Alan R. Liss, New York, 477494 (1981).

(4) Duax W. L. V. Cady, J. F. Griffin, D. C. Rohrer, and C .M. Weeks. Molecular conformation and protein binding affinity of progestins. J. Toxicol. Environ. Health 4::205–227 (1978)

(5) Burton G., M. D. Galigniana, S. de Lavallaz, A. L. Brachet -Cota, E. M. Sproviero, A. A. Ghini, C. P. Lantos and M. C. Damasco. Sodium-retaining activity of some natural and synthetic 21-deoxysteroids. Mol. Pharamacol 47:535–543 (1995).

(6) Arriza J., C. Weinberg, G. Cerelli, T. Glaser, B. Handelin, D, Housman, and R. Evans. Cloning of human mineralocorticoid receptor complementary DNA: structural and functional kinship with the glucocorticoid receptor. Science 237: 268–275 (1987).

(7) Teutsch G., F. Nique, G. Lemoine, F. Bouchoux, E. Cerede, D. Gofflo, and D. Philibert. General structure-activity correlations of antihormnones. Ann. N. Y. Acad. Sci. 761: 5–28 (1995).

(8) Grill H. J., Nickisch, P. E. Schulze, H. Laurent, W. Elger, A. Heubner, and K. Pollow: 3H-ZK91587: A new synthetic, highly specific ligand for mineralocorticoid receptor determination. J. Steroid Biochem 23-Suppl., 19S (1985).

(9) Sutanto W. and E. R. de Kloet. ZK91587: A novel synthetic antimineralocorticoid displays high affinity for corticosterone (Type I) receptors in the rat hippocampus. Life Sciences 43:1537–1543 (1988).

(10) Philibert D., R. Deraedt, and G. Teutsch. RU38486: a potent antiglucocorticoid in vivo. "IIIV International Congress of Pharmacology, Tokyo, Japan", Abstract (1981).

(11) Spitz I. M. and C. W, Bardin. Mefiprestone (RU486): a modulator of progestin and glucocorticoid action. N. Engl. J. Med. 329: 404–412 (1993).

(12) Brachet-Cota A. L. and G. Burton. An improved preparation of 11.19-oxidopregn 4-ene-3,20-dione and 6,19-oxidopregnan 4-ene-3,11,20-trione. Z. Naturforsch. Teil (B) 45: 711–715 (1990).

(13) Veleiro A. S. M. V. Nevado, M. C. Monteserin and G. Burton. Syntheses of 21-hydroxy-11,19-oxidopregn-4-ene-3,20-dione and 21-hydroxy-6,19-oxidopregn-4ene-3,20-dione. Steroids 60: 268–271 (1995).

(14) Galigniana M. D., G. P. Vincent, G. Burton, and C. P. Lantos. Features of the shuttle pair 11β-hydroxyprogesterone/11-ketoprogesterone. Steroids (1996), in press.

(15) Galigniana M. D. Stability study on renal type I mineralocorticoid receptor. Life Sci. 59: 511–521 (1996).

(16) Jordan V. C. and C. J. Dix. Effect of oestradiol benzonate, tamoxifen and monohydroxytamoxifen on immature rat uterine progesterone receptor synthesis and endometrial cell division. Journal of Steroid Biochemistry 11: 285–291 (1979).

(17) Krisman C. A method for the colorimetric estimation of glycogen with iodine. Anal. Biochem 4: 17–23 (1962).

(18) Fry J., C. Jones, P. Webkin, and J. Bridges. The enzymatic isolation of adult rat hepatocytes in a functional and viable state. Anal. Biocherm 71: 341–350 (1976).

(19) Granner D. and G. Tomkins. Metabolism of amino acids and amines. Tyrosine amino-transferase. Methods in Enzymology 17-A: 633–637 (1975).

(20) Gomez-Sanchez C. E. and E. P.Gomez-Sanchez. RU26988: a new tool for the study of the mineralocorticoid receptor. Endocrinology 113: 1004–1009 (1983).

(21) Funder J. W. Glucocorticoid receptors. J. Steroid Biochem Molec. Biol. 43: 389–394 (1992).

(22) Galigniana M. D., G. P. Vicent, C. P. Lantos and G. Burton. Ligand properties of 11,19-oxidoprogesterone: a preliminary report. An. Asoc. Quim. Argent. 81: 333–340 (1993).

(23) Krozowski Z. S. and J. F. Funder. Renal mineralocorticoid receptors and hippocampal corticosterone binding species have identical intrinsic steroid specificity. Proc. Natl. Acad Sci (USA) 80: 6056–6060 (1983)

(24) Kraujelis K. A. Ulinskaite, and V. Meilus. Transcortin in rat kidney: subcellular distibution of transcortin-synthesizing polyribosomes. J. Steroid Biochem. Molec. Biol. 38: 347 (1991).

What is claimed is:

1. A pharmaceutical composition comprising 21-hydroxy-6,19-oxidoprogesterone and pharmaceutically acceptable carrier therefor.

2. A method for the treatment or prophylaxis of a disease associated with an excess of glucocorticoids in a host which comprises administering an anti-corticoid effective amount of 21-hydroxy-6,19-oxidoprogesterone to the host.

3. The method according to claim 2, wherein the disease is Cushing's syndrome.

4. The method according to claim 2, wherein the disease is iatrogenic hypercortisolism.

5. The method according to claim 2, wherein the disease is depression.

* * * * *